United States Patent [19]
Nicholas

[11] Patent Number: 5,746,740
[45] Date of Patent: May 5, 1998

[54] SURGICAL BIOPSY FORCEPS APPARATUS

[75] Inventor: David A. Nicholas, Trumball, Conn.

[73] Assignee: United States Surgical Corporation, Norwalk, Conn.

[21] Appl. No.: 196,822

[22] Filed: Feb. 14, 1994

Related U.S. Application Data

[63] Continuation of Ser. No. 950,449, Sep. 23, 1992, abandoned.

[51] Int. Cl.$^6$ .................................................... A61B 17/39
[52] U.S. Cl. ............................ 606/52; 606/205; 606/207
[58] Field of Search ............................ 606/41, 42, 45.52, 606/205–208; 128/749–754

[56] References Cited

U.S. PATENT DOCUMENTS

| | | |
|---|---|---|
| 2,034,785 | 3/1936 | Wappler . |
| 2,790,437 | 4/1957 | Moore . |
| 3,585,985 | 6/1971 | Gould . |
| 3,895,636 | 7/1975 | Schmidt . |
| 3,964,468 | 6/1976 | Schulz ............................ 606/205 |
| 4,005,714 | 2/1977 | Hiltenbrandt ....................... 606/51 |
| 4,043,343 | 8/1977 | Williams . |
| 4,054,143 | 10/1977 | Bauer . |
| 4,128,099 | 12/1978 | Bauer . |
| 4,369,788 | 1/1983 | Goald . |
| 4,427,014 | 1/1984 | Bel et al. . |
| 4,512,343 | 4/1985 | Falk et al. ............................ 606/51 |
| 4,646,751 | 3/1987 | Maslanka . |
| 4,669,471 | 6/1987 | Hayashi . |
| 4,721,116 | 1/1988 | Schintgen et al. . |
| 4,763,668 | 8/1988 | Macek et al. . |
| 4,763,669 | 8/1988 | Jaeger . |
| 4,785,825 | 11/1988 | Romaniuk et al. . |
| 4,815,476 | 3/1989 | Clossick . |
| 4,819,633 | 4/1989 | Bauer et al. . |
| 4,880,015 | 11/1989 | Nierman . |
| 4,881,550 | 11/1989 | Kothe . |

(List continued on next page.)

OTHER PUBLICATIONS

The Mill–Rose Laboratories, Inc. GI Biopsy Forceps and Bronchial Biopsy Forceps Catalog, Copyright 1988.
The Technical Bulletin Castall E–343 A/B "Thermally Conductive Epoxy Conformal Coating".
The Valleylab SSE2L Instruction Manual.
The Technical Bulletin Castall E–343 A/B *Thermally Conductive Epoxy Conformal Coating*.
The Mill–Rose Laboratories, Inc. Gastrointestinal Biopsy Forceps and Bronchial Biopsy Forceps Catalog, Copyright 1988.
Cook OB/GYN® Catalog of Products for Obstetrics Gynecology and Surgery.
Storz, Operating Instruments Catalog, dated Mar. 1989.

*Primary Examiner*—Michael Peffley

[57] ABSTRACT

Apparatus including a frame; a generally elongated endoscopic portion connected to the frame and extending distally therefrom; a pair of jaw members cooperating with a distal end of the endoscopic portion, the jaw members disposed in opposing relation and being relatively pivotal about a common point between at least an open position and a closed position, each of the jaw members including: a distal portion including a first surface adapted for engaging tissue, the first surface having a recessed portion formed therein and a second surface being of smooth continuous construction; a proximal portion including pivot means adapted to cooperate with the inner rod member; and an intermediate portion being recessed relative to the distal portion such that upon contact of the jaw members, the intermediate portions are spaced apart from each other. The apparatus may further comprise means for rotating the endoscopic portion. In a preferred embodiment, the apparatus is a unipolar electrosurgical biopsy forceps and is provided with conducting means attachable to the frame and in electrical communication with a conductive endoscopic portion for receiving an electrical current from an electrical source. The jaw members are also electrically conductive. Electrical insulating means may be selectively disposed on the instrument for insulating predetermined portions thereof from electrical energy.

13 Claims, 4 Drawing Sheets

U.S. PATENT DOCUMENTS

| | | | |
|---|---|---|---|
| 4,887,612 | 12/1989 | Esser et al. ............................ 128/751 | |
| 4,896,678 | 1/1990 | Ogawa . | |
| 4,945,920 | 8/1990 | Clossick . | |
| 4,953,559 | 9/1990 | Salerno . | |
| 4,976,723 | 12/1990 | Schad . | |
| 4,977,900 | 12/1990 | Fehling et al. . | |
| 5,037,379 | 8/1991 | Clayman et al. . | |
| 5,037,433 | 8/1991 | Wilk et al. . | |
| 5,049,153 | 9/1991 | Nakao et al. . | |
| 5,052,402 | 10/1991 | Boncini et al. . | |
| 5,082,000 | 1/1992 | Picha et al. . | |
| 5,094,247 | 3/1992 | Hernandez et al. . | |
| 5,097,728 | 3/1992 | Cox et al. . | |
| 5,100,430 | 3/1992 | Avellanet et al. . | |
| 5,133,727 | 7/1992 | Bales et al. . | |
| 5,133,735 | 7/1992 | Slater et al. ............................ 606/205 |
| 5,147,373 | 9/1992 | Ferzli et al. ............................ 606/206 |
| 5,172,700 | 12/1992 | Bencini et al. . | |

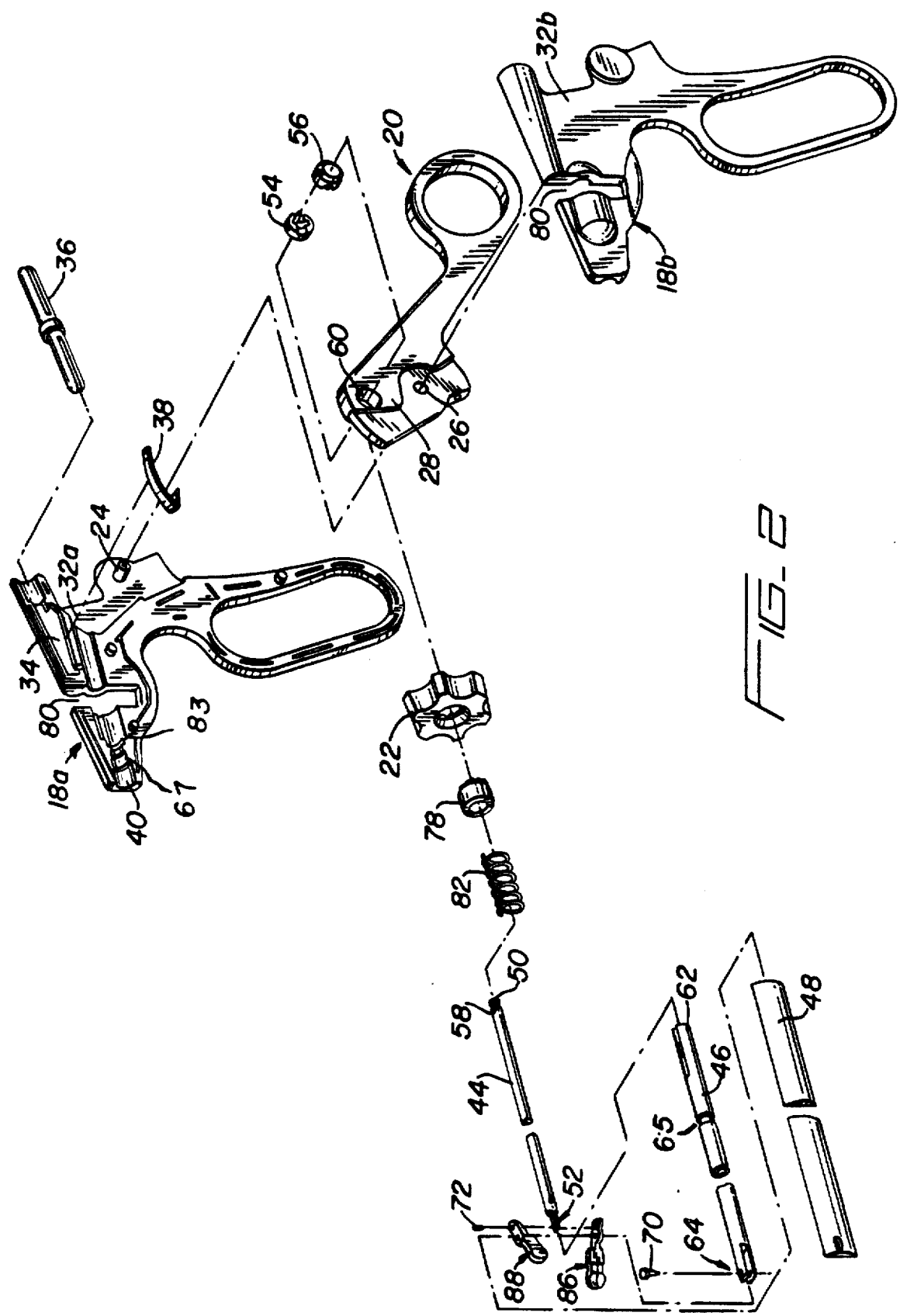

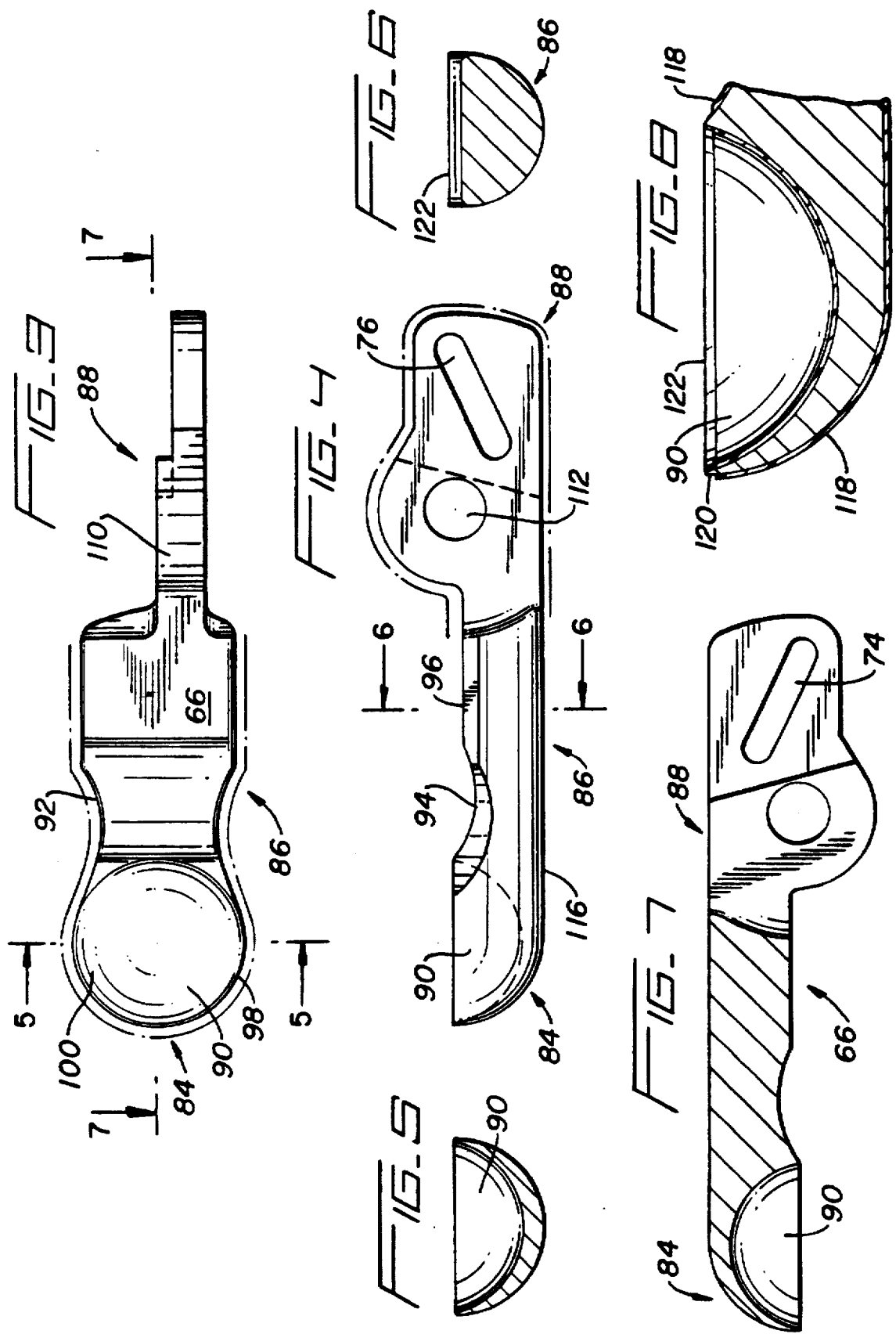

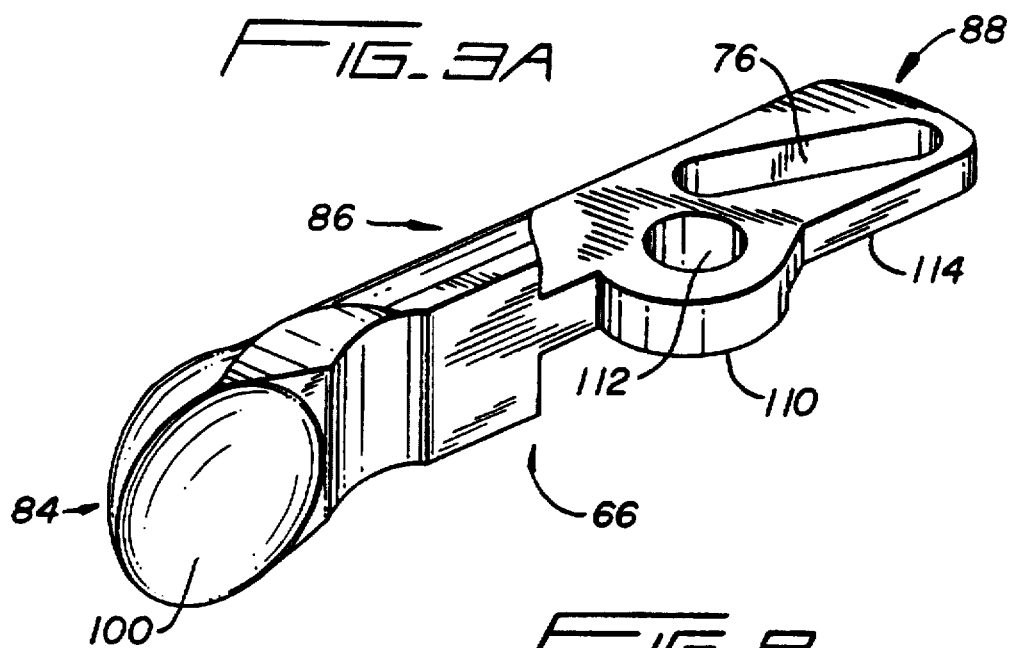
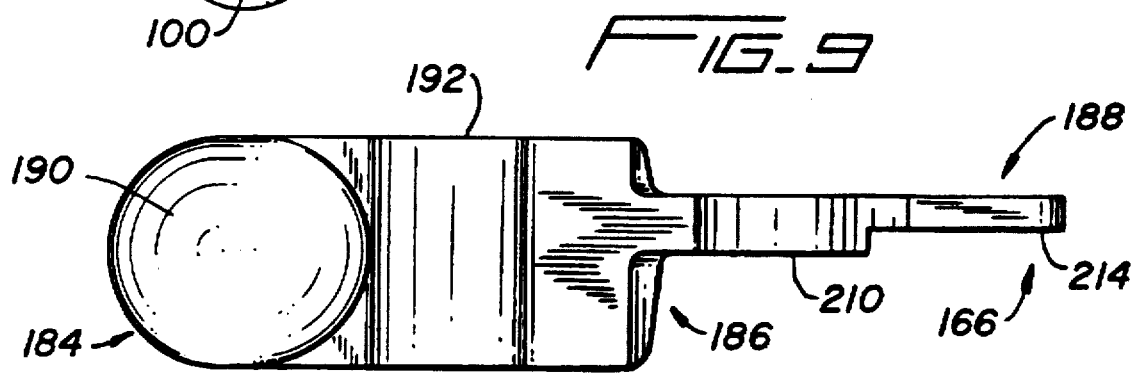
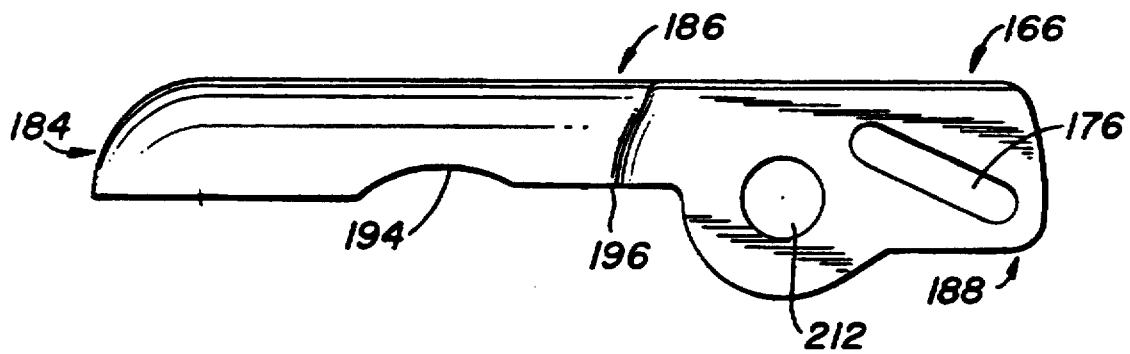

SURGICAL BIOPSY FORCEPS APPARATUS

This application is a continuation of U.S. Ser. No. 07/950,449, filed Sep. 23, 1992, (now abandoned).

BACKGROUND OF THE INVENTION

1. Field of the Invention

This invention relates to apparatus for performing surgical procedures and more particularly to apparatus for performing unipolar electrosurgical endoscopic or laparoscopic biopsies.

2. Description of the Related Art

In laparoscopic and endoscopic surgical procedures a small incision or puncture is made in the patient's body to provide access for a tube or a cannula device. Once extended into the patient's body, the cannula allows for insertion of various surgical instruments such as scissors, dissectors, retractors to perform surgery. The instruments need to be of sufficiently small size to fit through the cannula or tube and be manipulable and controllable from an end remote from the tool portion and outside the cannula.

A surgical biopsy is the excision of a small piece of tissue for microscopic examination, usually performed to establish a diagnosis. Endoscopic surgical biopsy of tissue has the advantages of other endoscopic/laparoscopic procedures in that it allows a portion of the tissue to be removed through a small incision or cannula, thus reducing the patient's healing time and reducing costs to the patient.

Although devices are known for removing specimens from the body, see, e.g., U.S. Pat. No. 5,037,379 to Clayman, these devices consist of bags that remove tissue or organs that have already been severed inside the body. Thus, an additional instrument is needed to separate the tissue and place it in the bag, requiring another incision in the body (to receive another cannula). Biopsy instruments on the other hand need to be able to sever the tissue and retain it for removal from the body for analysis. In endoscopic procedures, the jaws of the biopsy instruments must be able to tightly retain the sample after removal to ensure it does not slip during removal of the instrument through the cannula. In addition, since the cutting is performed remote from the surgeon, i.e., inside the body cavity, the instrument must be able to carefully remove and manipulate the specimen in order to limit contact with other parts of the body. Furthermore, since in endoscopic procedures, a camera is inserted into the cavity and the surgeon views the operation on a TV monitor, the instrument needs to be configured so as not to obstruct the camera's view.

To enhance the cutting function of the instrument, the tool portion, i.e., the jaws, can be conductive and have electrosurgical capabilities. Electrosurgery uses electrons to cut or coagulate tissue, in contrast with scalpels and like instruments which split tissue. Coagulation as used herein is a broad term which includes fulguration or desiccation, depending on the application. For general endoscopic and laparoscopic surgical procedures, a monopolar system (one in which the patient's body is part of the circuit) is common. With monopolar systems, electrical energy is delivered from an electrosurgical generator via a single conductor attached to the electrosurgical instrument and a return conductor is attached via a large surface to the patient, normally at the thigh. Without the proper connection, neuromuscular stimulation may occur. Monopolar (or unipolar) instruments are used primarily for cutting and fulguration. In electrosurgical cutting the objective is to heat the tissue so rapidly that cells explode into steam leaving a cavity in the cell matrix. The heat is dissipated in the steam and therefore it does not conduct through the tissue to dry out adjacent cells. When the electrode is moved and fresh tissue is contacted, new cells are exploded and the incision is made.

Although there currently exist some biopsy forceps, a need still exists for an improved biopsy forceps for endoscopic procedures which can effectively excise the tissue and remove it from the body cavity. A need also exists for such improved endoscopic biopsy forceps which has electrosurgical capabilities to enhance excising the tissue.

SUMMARY OF THE INVENTION

The present invention provides a novel biopsy forceps apparatus for endoscopic or laparoscopic surgery and includes a lightweight and easy to use apparatus which may be operated quickly and efficiently.

The apparatus includes a frame; a generally elongated endoscopic portion connected to the frame and extending distally therefrom; a pair of jaw members cooperating with a distal end of the endoscopic portion, the jaw members disposed in opposing relation and being relatively pivotal about a common point between at least an open position and a closed position, each of the jaw members including: a distal portion including a first surface adapted for engaging tissue, the first surface having a recessed portion formed therein and a second surface being of smooth continuous construction; a proximal portion including pivot means adapted to cooperate with the inner rod member; and an intermediate portion being recessed relative to the distal portion such that upon contact of the jaw members, the intermediate portions are spaced apart from each other.

The apparatus may further comprise means for rotating the endoscopic portion. The means includes a knob member circumferentially disposed about the frame and protruding radially outwardly from the frame through a slot formed therein.

In a preferred embodiment the apparatus is capable of performing electrosurgery. To facilitate this capability the endoscopic portion is electrically conductive and the apparatus is provided with conducting means attachable to the frame and in electrical communication with the endoscopic portion for receiving an electrical current from an electrical source. The jaw members are electrically conductive. Electrical insulating means may be selectively disposed on the instrument for insulating predetermined portions thereof from electrical energy. In one embodiment, the insulating means is applied to cover the jaw members such that all surface area of the jaw members is covered with the insulating material except for the tissue engaging surface. In another embodiment, the insulating means is applied to cover the jaw members such that all surface area of the jaw members is covered with the insulating material except for a portion of the tissue engaging surface. In a preferred embodiment, the apparatus is a unipolar electrosurgical biopsy forceps.

BRIEF DESCRIPTION OF THE DRAWINGS

Preferred embodiments of the invention are described hereinbelow with reference to the drawings wherein:

FIG. 2. is an exploded view with parts separated of the instrument of FIG. 1;

FIG. 3 is a side plan view of the jaw member of the instrument of FIG. 1;

FIG. 3A is a perspective view of the jaw of FIG. 3;

FIG. 4 is a top plan view of the jaw member of the instrument of FIG. 1;

FIG. 5 is a cross-sectional end view taken along lines 5—5 of FIG. 3;

FIG. 6 is a cross-sectional view taken along lines 6—6 of FIG. 4;

FIG. 7 is a cross-sectional view taken along lines 7—7 of FIG. 3;

FIG. 8 is a partial view of a cross section of the distal end of a jaw member of the present invention;

FIG. 9 is a side plan view of an alternative embodiment of the jaw member of the present invention; and FIG. 10 is a bottom plan view of the jaw member of FIG. 9.

DETAILED DESCRIPTION OF THE PREFERRED EMBODIMENTS

Figure 1:
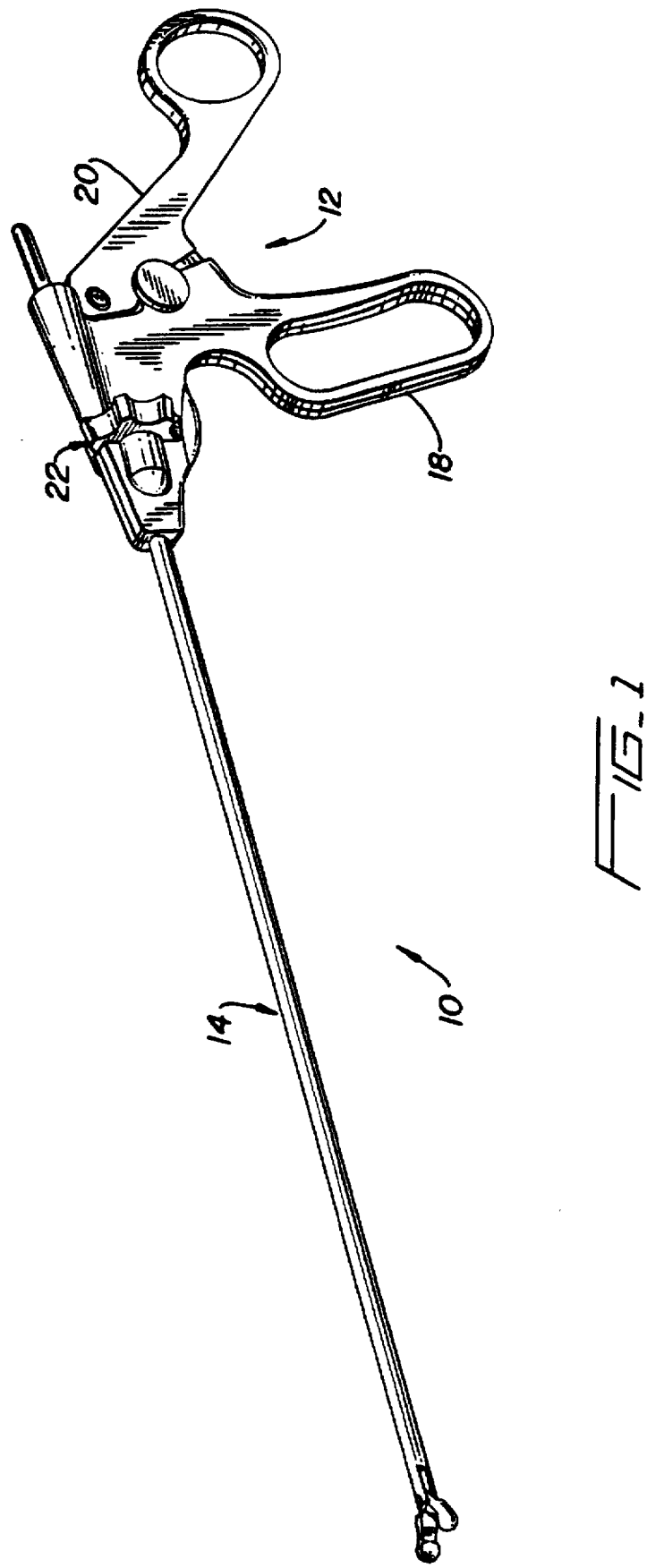
FIG. 1 is a perspective view of the electrosurgical instrument of the present invention.

Referring initially to FIG. 1, the endoscopic electrosurgical biopsy instrument of the present invention, designated by reference numeral 10, will now be described in detail. Apparatus 10 includes handle assembly 12, elongated endoscopic portion 14 extending from handle assembly 12, and a pivoting jaw mechanism 16 mounted at a distal end portion of the endoscopic portion. Handle assembly 12 includes stationary handle 18 and pivoting handle 20 mounted thereto such that movement toward stationary handle 18 closes jaw mechanism 16 and movement away from stationary handle 18 opens jaw mechanism 16. The operation of jaw mechanism 16 to excise tissue may be performed either with or without operation of the electrosurgical feature of the invention which will be described in further detail below. Also provided on handle assembly 12 is knurled collar 22 for rotation of the entire endoscopic portion 14 and jaw mechanism 16 described below.

As best seen in FIG. 2, stationary handle 18 is constructed of split sections 18a and 18b being joined by the interfitting of a series of corresponding bosses and apertures. Pivoting handle 20 is mounted between sections 18a and 18b by way of pivot post 24 passing through bore 26. The range of motion of pivoting handle 20 is governed by raised contoured step portions 28 contacting slot walls 32a and 32b which define a slot in the distal end of handle 20. Each of the sections 18a and 18b are formed with a portion of a stepped bore 40 which is provided therein for accommodating various components of the subject invention, all of which will be described in greater detail hereinbelow.

Each of the opposed sections 18a and 18b of handle assembly 12 are also formed with a portion of longitudinal channel 34 for maintaining plug adapter member 36. Plug member 36 is provided for connecting apparatus 10 to an electrical generator, in order to perform electrosurgical procedures at the surgical site. One such generator is the Valleylab SSE2L described in *Valleylab SSE2L INSTRUCTION MANUAL* the contents of which are incorporated by reference herein in their entirety. Leaf spring 38 is disposed in handle assembly and is in electrical contact with the plug member 36. In order to protect the user from electrical shock during electrosurgical procedures, handle assembly 12 is preferably constructed of a nonconducting material, for electrical insulation.

Endoscopic portion 14 includes inner rod member 44, tubular section 46 and tubular cover section 48. Cover section 48 is preferably made of a shrink wrap insulating material to provide further protection from electrical shock.

Inner rod member 44 has opposed proximal and distal ends 50 and 52, respectively, with proximal end 50 connected to pivotal handle 20. The connection is accomplished by a pair of opposed clips 54 and 56 each having semi-annular grooves formed therein which are adapted to fit over and retain disk-shaped head portion 58 formed at proximal end 50 on inner rod 44. Proximal end 50 passes through slot 51 formed in pivotal handle 20. The entire assembly is retained in bore 60 provided in pivoting handle 20. Inner rod member 44 is thereby movable in an axial direction in response to movements of pivoting handle 20 thereby opening and closing the jaw mechanism 16.

Tubular section 46 has opposed proximal and distal ends 62 and 64, respectively, and is mounted for reciprocating coaxial movement with respect to the inner rod member 44. Specifically, tubular section 46 has annular groove 65 which seats on raised semi-annular portions 67 formed along stepped bore 40 formed by split sections 18a and 18b. At distal end 64, tubular section 46 terminates in a clevis in which cooperating jaws 66 and 68 are pivotably mounted by way of pivot pin 70. Jaws 66 and 68 are also mounted to inner rod member 44 at distal end 52 by pin 72. Specifically, pin 72 extends through camming slots 74 and 76 formed in jaws 66 and 68, respectively (See FIGS. 4 and 7). In operation, upon squeezing handle 20 toward handle 18, inner rod 20 is pulled proximally causing pin 72 to travel proximally and along camming slots 74 and 76 thereby urging jaws 66 and 68, respectively, to a closed position. When handle 20 is pulled proximally, pin 72 travels distally and slides along camming slots 74 and 76 to urge jaws 66 and 68 to the open position as shown in FIG. 1.

Apparatus 10 of the subject invention further comprises a mechanism for rotating the endoscopic portion 14 about its longitudinal axis and relative to the handle assembly 12. This mechanism comprises an annular bushing 78 which is concentrically mounted within operative collar 22. Collar 22 is mounted within port 80 formed in handle assembly 12. Bushing 78 is maintained against collar 22 by coil spring 82 disposed in a section of bore 40. Spring 82 which is biased against shoulder portions 83 of split sections 18a and 18b, acts to bias bushing 78 toward the proximal end of bore 40. Thus, rotation of collar 22 rotates the endoscopic portion 14 and attached jaw mechanism 16 to allow reorientation of the jaws. As is readily apparent, the jaws can be rotated a full 360°.

Referring to FIGS. 3–8, the jaw member of the present invention is illustrated in the form of biopsy forceps jaw member 66 adapted to grasp tissue. Since opposing jaw members 66 are identical the following description will refer to a single jaw. It should be borne in mind, however, that the description applies to the opposing jaw member as well. One material which has been found to be particularly suited for forming jaw 66 is a ferrous-nickel alloy of approximately 2% nickel content having a hardness of 43–48 on the Rockwell hardness C-scale. The material is preferably plated with nickel by a non-electrolytical process such as sputtering or the like. Clearly other materials can be utilized for the jaws. Jaw member 66 has a distal portion 84, an intermediate portion 86 and a proximal portion 88. Distal portion 84 includes a tissue grasping portion such as hemispherical cup portion 90 formed in the solid material. The hemispherical cup portions of both jaws cooperate to form a spherical specimen receiving cavity when the jaws are closed. Intermediate portion 86 is arcuately contoured at neck 92, adjacent cup 90, as best seen in FIG. 3. Neck 92 also has arcuate portion 94 which, inter alia, serves to provide a smooth transition to straight portion 96 at which point the thickness of intermediate portion 86 is less than that of distal portion 84, as is best illustrated in FIG. 4 and in the cross-sectional view in FIG. 6. This smaller dimension of intermediate portion 86 relative to distal portion 84 allows opposing jaws 66 to contact each other at circumferential perimeter 98 only, thereby preventing contact of jaws 66 along intermediate portion 86 thereof. A cavity is formed by the corresponding hemispherical cup shaped portions 90 coming together during opposing contact of jaws 66 which facilitates retention of excised tissue samples for removal and analysis.

As best seen in FIG. 3A, proximal end 88 is preferably disposed in a plane substantially transverse to a plane defined by tissue gripping face 100 of distal portion 84. Step portion 110 is provided having pivot hole 112 for mounting opposing jaw members 66 on tubular section 46 as described above. Lower end portion 114 has diagonal camming slot 76 formed therethrough for cooperatively mounting jaw 66 to inner rod 44 at distal end 52 as described above.

Jaw 66 is further provided with smoothly formed straight outer edge wall 116 with a curved cross-section as illustrated in FIG. 6. This configuration allows the distal end of apparatus 10 to be manipulated in confined areas of the patient's body and obtain tissue samples or perform electrosurgery therein with minimal traumatization of non-targeted tissue.

In an alternative embodiment, the jaw members are provided with an oblong cup portion such as oblong cup 190 located on distal portion 184 of jaw member 166, shown in FIG. 9. Jaw member 166 has a distal portion 184, an intermediate portion 186 and a proximal portion 188. Distal portion 184 includes a tissue grasping portion such as oblong cup portion 190 formed in the solid material. The oblong cup portions of both jaws cooperate to form a specimen receiving cavity when the jaws are closed. Intermediate portion 188 has a straight construction at neck 192, adjacent cup 190. Neck 192 also has arcuate portion 194 which, inter alia, serves to provide a smooth transition to straight portion 196 at which point the thickness of intermediate portion 186 is less than that of distal portion 184, as is best illustrated in FIG. 10. In this regard, jaw member 166 is the same as jaw member 66.

In one preferred embodiment, when apparatus 10 is used for electrosurgical procedures, jaws 66 are coated with an electrically insulating material over their entire surface except for tips 120 so that a more precise cutting may be performed. In another embodiment, jaws 66 are partially coated with the insulating material, for example, as in FIG. 8 so that only circumferential perimeter 98 is electrically conductive or as in FIG. 4 shown in phantom line around proximal portion 88 so that intermediate portion 86 and distal portion 84 are electrically conductive. In another embodiment, jaws 66 are not insulated at all. In embodiments where jaws 66 are to be insulated, one preferred material is, for example, CASTALL E-343 A/B, a thermally conductive epoxy conformal coating. CASTALL's material properties and methods of use are explained in detail in *TECHNICAL BULLETIN CASTALL E-343 A/B Thermally Conductive Epoxy Conformal Coating* a publication of Castall, Incorporated, East Weymouth, Mass., the entire contents of which are hereby incorporated by reference. Other available conventional coatings which are also suitable are Hardcoat, Mica and Mylar. The coating material selected may be sprayed on with conventional spray equipment.

In any case, whether insulation is provided on jaws 66 or not, apparatus 10 is provided with tubular cover 48 which is made of a non-conducting material, for example polyvinylchloride (PVC). One preferred method of applying cover 48 is by heat shrinking it onto and around tubular section 46.

Except where otherwise noted above, the materials utilized in the components of the apparatus described herein generally include such materials as polycarbonate for housing sections and related components, and stainless steel for such components which transmit forces and electricity. One preferred polycarbonate material is LEXAN brand polycarbonate available from the General Electric Company. Other specific preferred materials such as nylon or glass filled nylon (for strength) may also be utilized. However, equivalent alternative materials will readily come to the mind of those skilled in the art.

In operation, apparatus 10 having a preselected amount of insulation coated on jaws 66 is connected by way of electrical wiring (not shown) to an electrical generator, such as the Valleylab SSE2L, preferably having multiple waveform producing capabilities, e.g., cut, coag or blend. The instrument is inserted into a trocar cannula placed in the patient and thereby into the surgical site. The appropriate mode of electrosurgical energy is selected on the generator and the surgeon manipulates the instrument into position and using pivoting handle 20 grasps the desired tissue thereby making electrical contact with the tissue and achieving cutting or fulguration as desired. The incised portion is then retained in the cup-shaped portion formed by the closed jaws and removed along with the instrument through the cannula for analysis.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. Apparatus for endoscopic or laparoscopic electrosurgery which comprises:
   a) a frame;
   b) a generally elongated endoscopic portion connected to said frame and extending distally therefrom, said endoscopic portion being electrically conductive said endoscopic portion including:
      i) an inner rod member positioned within said endoscopic portion;
      ii) an outer tubular member secured to said frame and surrounding said inner rod member such that said inner rod member is slidable within said outer tubular member;
   whereby said inner rod member is slidable between a first position and a second position;
   c) conducting means attachable to said frame and in electrical communication with said endoscopic portion for receiving an electrical current from an electrical source;
   d) a pair of jaw members mounted at a distal end of said endoscopic portion, disposed in opposing relation and being relatively pivotable about a common point between at least an open position and a closed position, at least one of said jaw members being electrically conductive and each of said jaw members including:
      i) a distal portion including a first surface adapted for engaging tissue, said first surface having a recessed portion formed therein and a second surface being of smooth continuous construction;

ii) a proximal portion pivotably attached to said inner rod member such that said jaw members are pivotable between said open and said closed positions;

iii) an intermediate portion including a first section being recessed relative to said first surface of said distal portion such that said opposing jaw members are contactable with one another along said distal and intermediate portions only at said first surfaces of said respective distal portions for engaging tissue, said intermediate portion of each of said jaw members remaining spaced apart from each other, said intermediate portion further including an arcuate cross sectional dimension along a periphery thereof which is transverse to said first section of said intermediate portion.

2. Apparatus for endoscopic or laparoscopic electrosurgery according to claim 1 further comprising electrical insulating means selectively disposed on said apparatus for insulating predetermined portions thereof from electrical energy.

3. Apparatus for endoscopic or laparoscopic electrosurgery according to claim 2 wherein said insulating means is applied to cover said jaw members such that all surface area of said jaw members is covered with said insulating material except for said tissue engaging surface.

4. Apparatus for endoscopic or laparoscopic electrosurgery according to claim 2 wherein said insulating means is applied to cover said jaw members such that all surface area of said jaw members is covered with said insulating material except for a portion of said tissue engaging surface.

5. Apparatus for endoscopic or laparoscopic electrosurgery according to claim 2 wherein said electrical insulating means is a thermally conductive epoxy conformal coating.

6. Apparatus for endoscopic or laparoscopic electrosurgery according to claim 1 wherein said apparatus further comprises means for rotating said endoscopic portion.

7. Apparatus for endoscopic or laparoscopic electrosurgery according to claim 6 wherein said rotating means comprises a knob member circumferentially disposed about said outer tubular member and protruding radially outward from said frame through a slot formed therein.

8. Apparatus for endoscopic or laparoscopic electrosurgery according to claim 1 wherein said apparatus is unipolar.

9. A tool adapted to be connected to an electrosurgical endoscopic or laparoscopic instrument having a frame; a generally elongated endoscopic portion connected to said frame and extending distally therefrom, said endoscopic portion being electrically conductive; conducting means attachable to said frame and in electrical communication with said endoscopic portion which are in electrical communication with said tool, for receiving an electrical current from an electrical source and conducting said electrical current to said endoscopic portion which in turn conducts said electrical current to said tool; which tool comprises a pair of pivotally cooperating opposing jaw members, each of said jaw members operatively associated with said endoscopic portion comprising:

a) a proximal portion having means for pivotally mounting said jaw to a distal end of said generally elongated endoscopic portion;

b) a distal portion including a first surface adapted for engaging tissue, said first surface having a recessed portion formed therein and a second surface being of smooth continuous construction, such that when said jaw member is attached to said electrosurgical instrument said recessed portion opposes a recessed portion of a corresponding jaw member; and c) an intermediate portion including a first section being recessed relative to said first surface of said distal portion, such that said opposing jaw members are contactable with one another along said distal and intermediate portions only at said first surfaces of said respective distal portions for engaging tissue, said intermediate portion of each of said jaw members remaining spaced apart from each other, said intermediate portion further including an arcuate cross sectional dimension along a periphery thereof which is transverse to said first section of said intermediate portion.

10. Tool for use with an electrosurgical endoscopic or laparoscopic instrument according to claim 9 further comprising electrical insulating means selectively disposed on said instrument for insulating predetermined portions thereof from electrical energy.

11. Tool for use with an electrosurgical endoscopic or laparoscopic instrument according to claim 10 wherein said insulating means is applied to cover said jaw members such that all surface area of said jaw members is covered with said insulating material except for said tissue engaging surface.

12. Tool for use with an electrosurgical endoscopic or laparoscopic instrument according to claim 10 wherein said insulating means is applied to cover said jaw members such that all surface area of said jaw members is covered with said insulating material except for a portion of said tissue engaging surface.

13. Tool for use with an electrosurgical endoscopic or laparoscopic instrument according to claim 10 wherein said electrical insulating means is a thermally conductive epoxy conformal coating.

\* \* \* \* \*